| United States Patent [19]
Bebbington | [11] 4,145,349
[45] Mar. 20, 1979 |
|---|---|

[54] PROCESS FOR THE PRODUCTION OF SACCHARINE

[75] Inventor: Anthony J. Bebbington, Toronto, Canada

[73] Assignee: Commercial Organics Limited, Montreal, Canada

[21] Appl. No.: 862,220

[22] Filed: Dec. 19, 1977

[51] Int. Cl.$^2$ ............................................. C07D 277/64
[52] U.S. Cl. ................................. 260/301; 260/304 A
[58] Field of Search ............................. 260/304 A, 301

[56] References Cited

U.S. PATENT DOCUMENTS 4,076,721  2/1978  Loike ..................................... 260/301

FOREIGN PATENT DOCUMENTS 0158550  6/1975  Czechoslovakia.
1163934  9/1969  United Kingdom.

OTHER PUBLICATIONS

Hagyard, T. and W. Meachen (Reporters), B10S Trip #3110, "Manufacture of Saccharin and its Intermediates," 1947.

Primary Examiner—Donald G. Daus
Assistant Examiner—Lisa Jones
Attorney, Agent, or Firm—Ridout & Maybee

[57] ABSTRACT

This invention relates to a process of producing saccharin by reacting o-chlorobenzoic acid with sodium sulfite, esterifying it with methanol, and then treating the o-sulfobenzoic acid methyl ester with thionyl chloride as a chlorinating agent, the improvement comprising, in combination, salting out the whole of the o-sulphobenzoic acid from the solution of its salt in the form of potassium o-carboxy benzene sulfinate by the addition of hydrochloric acid and potassium chloride, removing the inorganic salt form prior to chlorination, and using no more than a two fold excess of chlorinating agent.

3 Claims, No Drawings

PROCESS FOR THE PRODUCTION OF SACCHARINE

FIELD OF THE INVENTION

This invention relates to the preparation of saccharine.

BACKGROUND OF THE INVENTION

Saccharine has been used as a substitute for sugar as a sweetening agent for about ninety years. Its use was initially limited to those unable to tolerate sugar in their diet, but its consumption has recently been greatly increased by the rising popularity of low-calorie foods and beverages. Although other artificial sweeteners have been developed and marketed, doubts have been raised as to their safety, and saccharine has retained a dominant position in the market. Recently, doubts have also been raised as to the safety of saccharine itself, leading to restrictions upon its use in various countries.

The safety of saccharine has become suspect because laboratory tests have shown in some cases that rats fed very large quantities of saccharine have shown a tendency to develop cancer of the bladder. However, further tests have suggested that these results may be due to an as yet unidentified impurity in the saccharine.

The traditional method for making saccharine was developed in 1879 by Fahlberg and Remsen, and consists of oxidizing o-toluene sulfonamide (OTSA) by use of an oxidizing agent such as potassium permanganate. This method is still used today by many saccharine producers. The safety of residual OTSA in saccharine has been questioned, and other potentially dangerous impurities could possibly be present. A second process for manufacturing saccharine, developed in Germany in the late nineteenth century, was commercialized in the early nineteen fifties. This process starts from phthalic anhydride and proceeds via eight steps of synthesis, involving five isolations of intermediates, to saccharine. The development of this process was long and difficult, and its complexity and the large number of steps involved makes it difficult to operate economically.

During the Second World War, a further process for the synthesis of saccharine was developed in Germany as a result of shortages of raw materials required for the Remsen-Fahlberg process. In this further process, o-chlorotoluene was oxidized by the use of dichromate to yield o-chlorobenzoic acid, and following the substitution of chlorine by an $SO_3H$ group, the potassium salt of o-sulfobenzoic acid was isolated. After esterification, the methyl ester of o-sulfobenzoic acid was converted using sulfuryl chloride to the corresponding sulfonyl chloride which was treated to provide saccharine using ammonium hydroxide and a mineral acid. The disadvantage of this process was a low yield (even in theory only 46.1% related to the o-chlorotoluene) and the high cost. The process was not therefore competitive under normal commercial conditions.

In Czechoslovakian Author's Certificate No. 158,550 issued June 15, 1975 to Brezina et al, there is described a variant upon the wartime German process described above, said to improve its yield. o-Chlorotoluene is again converted to o-chlorobenzoic acid by any of several known processes. The sodium salt of the o-chlorobenzoic acid is converted to the disodium salt of o-sulfobenzoic acid by the use of sodium sulfite in aqueous solution catalyzed by copper salts. The disodium salt mixed with inorganic impurities, after azeotropic dehydration with o-dichlorobenzene, is reacted in the same solvent with chlorosulfonic acid and methanol to obtain the methyl ester of o-sulfobenzoic acid which ester is treated with a three times molar excess of phosgene (or the more expensive but safer thionyl chloride) to yield methoxycarbonylbenzene-o-sulfonylchloride, which is subsequently converted, using ammonium hydroxide, to the ammonium salt of saccharine, from which saccharine or its salts may be obtained by known methods.

I have been quite unable to reproduce the results reported in the Czechoslovakian Author's Certificate, whilst I have found a problem with the wartime German technique to be that, in order to obtain good yields of saccharine, it is necessary to use a large (3M) excess of chlorinating agent, even when phosgene or thionyl chloride are substituted for sulfuryl chloride, and the reaction is catalyzed by a tertiary amide, as suggested in the Czechoslovakian Author's Certificate; as the amount of chlorinating agent used is increased, the organic impurities in the product increase substantially.

The object of the present invention is to provide a further improvement over the wartime German and Czechoslovakian processes discussed above, enabling the economic preparation of saccharine by a route which minimizes the possibility of the final product being contaminated by any known carcinogens, and does not require it to be freed from substantial amounts of organic contaminants whose safety may be suspect.

SUMMARY OF THE INVENTION

I have now found that excellent yields of saccharine of good purity may be obtained using only a small excess of chlorinating agent. Contrary to the teaching of the Czechoslovakian Author's Certificate, which suggests that salting out of the o-sulfobenzoic acid to obtain is monopotassium salt is undesirable because of the non-quantitative nature of this reaction, I have found that, in spite of the low purity of the salt thus obtained, which is heavily contaminated with potassium chloride, the use of this step renders it possible easily to separate the inorganic salts produced during the subsequent production of o-sulfobenzoic acid methyl ester prior to chlorination of the latter. Surprisingly, this separation enables a high yield to be obtained in the subsequent chlorination step without use of a large excess of the chlorination agent, and this in turn results in greatly improved purity of the saccharine produced by the process.

Thus according to the invention in a method of producing saccharine comprising the steps of sulfonating o-chlorobenzoic acid with sodium sulfite in an aqueous solution in the presence of a copper salt to produce o-sulphobenzoic acid, which is recovered from the solution as an alkali metal salt which is dried and dehydrated to provide o-sulphobenzoic acid endo-anhydride, reacting the latter with methanol to provide o-sulphobenzoic acid methyl ester, treating the o-sulphobenzoic acid methyl ester with excess phosgene or thionyl chloride in the presence of a catalytic amount of a tertiary amide to provide methoxycarbonylbenzene-o-sulfonyl chloride, and reacting the latter compound with ammonium hydroxide and then acidifying to provide saccharine, the process is improved by, in combination, salting out substantially the whole of the o-sulphobenzoic acid from the solution of its salt in the form of potassium o-carboxybenzene sulfonate by the addition of hydrochloric acid and potassium chloride, removing the inorganic salts formed during dehydration of the potassium salt prior to chlorination of the o-sulfobenzoic acid methyl ester and using no more than a twofold excess of phosgene or thionyl chloride, preferably only a 1.5 fold excess. In order to facilitate the salting out process, the treatment of the o-chlorobenzoic acid should be such as to provide a high concentration of o-sulfobenzoic acid in the reaction mixture.

DESCRIPTION OF THE PREFERRED EMBODIMENT

Further features of the invention will become apparent from the following annotated description of an Example representing a preferred embodiment thereof.

Example

To 151 gm $Na_2SO_3$ in 300 ml $H_2O$, add 150 gm o-chlorobenzoic acid. Neutralize with sodium carbonate or hydroxide, and add as catalyst 10 gm $CuSO_4.5H_2O$. Make up the volume with water to 500 ml pH = 6.0–6.5, heat to 150° C. in a pressure vessel and hold at this temperature for 9 hours with stirring. The pH during sulfonation could be maintained at 6.0–6.5 by automatic addition of NaOH or $Na_2CO_3$, thus allowing the use of a stainless steel reactor instead of the glass lined reactor recommended. However, the pH must not be allowed to rise over 6.5 as this facilitates the formation of salicylic acid (OH replacement instead of $SO_3$ replacement), which can not be tolerated.

The reaction mixture is cooled to 20° C. and unreacted o-chlorobenzoic acid is filtered out, the filter cake being washed with 50 ml water, and the washings combined with the filtrate. The o-chlorobenzoic acid recovered (about 8 g dry weight) could be recycled. 143 gm KCl is added to the filtrate over 1 hour, and after 2 hours mixing 77 ml HCl is added. The mixture is cooled to 10° C. and mixed for 2 hours. If the crystals gell, a minimum of water may be added. The crystals are removed by filter or centrifuge, washed with 200 ml of a saturated aqueous solution of KCl, and dried at a temperature not exceeding 120° C. The product is 73% potassium o-carboxybenzene sulfonate, the remainder being inorganic salts, mainly potassium chloride. This corresponds to an actual potassium o-carboxybenzene sulfonate content of 207.5 gm and a yield of 95%.

The concentrations of the reagents during the sulfonation are selected so as to provide a high (33.4%) o-sulfobenzoic acid concentration in the reaction mixture obtained. This facilitates the subsequent 'salting out' of the potassium salt and is desirable in order to ensure a high recovery of the salt. An o-sulfobenzoic acid content of at least 25% and preferably at least 30% is desirable.

The potassium o-carboxybenzene sulfonate is carefully dried and finely divided and mixed with 795 ml dichloroethane. The temperature is raised to 30° C., and 86.3 ml (1.5 M eq.) of chlorosulfonic acid in 170 ml dichloroethane are added whilst mixing over a period of 1 hour. The temperature is raised to reflux (85° C.), in not less than 1 hour, and refluxing is continued for 1 hour. During this process, HCl gas is discharged. The reaction mixture is cooled to 30° C., and 70 ml methanol (2 M eq.) is added and mixed for 2 hours at 50° C. The solids (inorganic salts) are removed by centrifugation or filtration and washed with dichloroethane, the washings being combined with the solvent phase. Excess methanol is removed from the latter by distillation, and 94.1 ml of thionyl chloride (1.5 M eq.) is added together with 1.7 ml of N,N-dimethylformamide, followed by refluxing for 4½ hours. During this refluxing $SO_2$ and HCl are evolved. The excess thionyl chloride is distilled off and can be recycled, leaving a solution of methoxycarbonylbenzene-o-sulfonyl chloride in dichloroethane. It will be understood that the chlorination may be catalyzed by catalytic amounts of other tertiary amides in place of N,N-dimethylformamide.

It should be noted that the removal of solids prior to the chlorination step is an essential feature of the process. The solids are very fine, and filter slowly. They do, however, settle well and can be removed by a stacked disc or bowl centrifuge although filtration is preferred. The solids must be washed or extracted to remove entrained methyl o-sulfobenzoate. Dichloroethane is not the only suitable solvent; other solvents that could be used include chloroform (b.p. 61° C.) and S-tetrachloroethane (b.p. 140°–150° C.). As the chlorinating agent, phosgene could be used to replace thionyl chloride, but due to the toxicity of phosgene, thionyl chloride is preferred.

The quantity of chlorinating agent used is important. Some excess is required in order to obtain a high yield, but I find that as the excess becomes larger, the quality of the saccharine obtained in the next stage of the process from the methoxycarbonylbenzene-o-sulfonyl chloride deteriorates with an increasing content of organic contaminants. Thus with the use of 1.1 M eq. of thionyl chloride the saccharine obtained has, without purification, a melting point the same as that of pure saccharine, whilst with the use of 1.7 M eq. of thionyl chloride the product is discolored and the melting point is depressed by 3° C. from that of pure saccharine. The use of 2 M eq. of thionyl chloride brings further deterioration, the product being heavily discolored. The German and Czechoslovakian processes discussed above specify the use of approximately 3 M eq. of chlorinating agent in order to obtain satisfactory yields, whereas with the present process good (75%) yields can be obtained using as little as 1.2 or even 1.1 M eq., with a maximum yield of approximately 83% using about 1.5 M eq. of thionyl chloride.

The solution of methoxycarbonylbenzene-o-sulfonyl chloride in dichloroethane is added to a mixture of 266 ml aqua ammonia (4.5 M eq.) and 660 ml water, at a rate such that the temperature does not exceed 35° C., with thorough mixing. Mixing is continued for 2 hours at 35° C., followed by filtration to remove the small amount of solids formed. The two solvent phases are allowed to separate, and the dichloroethane is drained off for distillation and re-use. 120 ml of hydrochloric acid is added over a period of 1 hour to bring the solution to pH 1, with the temperature being kept below 40° C. The solution is cooled to 20° C. and mixed for 1 hour, before being filtered to collect the crude saccharine which is precipitated. The saccharine may then be further purified and converted to calcium or sodium saccharine, as desired, by conventional methods.

What I claim is:

1. In the method of producing saccharine comprising the steps of sulfonating o-chlorobenzoic acid with sodium sulfite in aqueous solution in the presence of a copper salt to produce o-sulfobenzoic acid, recovering from the solution and drying the o-sulfobenzoic acid as an alkali metal salt, dehydrating the salt to provide o-sulphobenzoic acid endoanhydride and reacting the latter with methanol to provide o-sulfobenzoic acid methyl ester, treating the o-sulfobenzoic acid methyl ester with excess of thionyl chloride as, chlorinating agent, in the presence of a catalytic amount of a tertiary amide, to provide methoxycarbonylbenzene-o-sulfonyl chloride, and reacting the latter compound with ammonium hydroxide and then acidifying to provide saccharine, the improvement comprising, in combination, salting out substantially the whole of the o-sulphobenzoic acid from the solution of its salt in the form of potassium o-carboxybenzene sulfonate by the addition of hydrochloric acid and potassium chloride, removing the inorganic salt formed during dehydration of the potassium salt prior to chlorination of the o-sulfobenzoic acid methyl ester, and using no more than a twofold excess of the chlorinating agent.

2. A process according to claim 1, wherein no more than about a 1.5 fold excess of chlorinating agent is utilized.

3. A process according to claim 2, wherein the concentrations of the reagents used in the sulfonation of the o-chlorobenzoic acid are selected so as to provide in the reaction mixture a concentration of the sulfonated product equivalent to a cncentration of at least 30% of o-sulphobenzoic acid.

* * * * *